United States Patent [19]

Le Count et al.

[11] 3,959,486

[45] May 25, 1976

[54] METHOD FOR PRODUCING β-ADRENERGIC BLOCKAGE WITH ALKANOLAMINE DERIVATIVES

[75] Inventors: David James Le Count, Congleton; Christopher John Squire, Cheadle Hulme, both of England

[73] Assignee: Imperial Chemical Industries Limited, London, England

[22] Filed: Jan. 7, 1974

[21] Appl. No.: 431,297

Related U.S. Application Data

[63] Continuation of Ser. No. 145,897, May 21, 1971, abandoned.

[30] Foreign Application Priority Data

May 27, 1970 United Kingdom............... 25529/70
Nov. 20, 1970 United Kingdom............... 55246/70

[52] U.S. Cl. .............................................. 424/324
[51] Int. Cl.² ...................................... A61K 31/165
[58] Field of Search ............ 260/559, 562; 424/330, 424/324

[56] References Cited

UNITED STATES PATENTS

| | | | |
|---|---|---|---|
| 3,466,325 | 9/1969 | Brandstrom .................... | 260/501.17 |
| 3,483,221 | 12/1969 | Wilhelm et al. ............... | 260/326.14 |
| 3,562,297 | 2/1971 | Howe et al........................... | 260/562 |
| 3,574,749 | 4/1971 | Howe et al........................... | 260/562 |
| 3,634,511 | 1/1972 | Howe et al........................... | 260/562 |
| 3,641,152 | 2/1972 | Shavel et al. ...................... | 260/562 |
| 3,663,607 | 5/1972 | Barrett et al....................... | 260/559 |

*Primary Examiner*—Donald B. Moyer
*Attorney, Agent, or Firm*—Cushman, Darby & Cushman

[57] ABSTRACT

New 1-amino-3-carbamoylalkoxyphenoxypropan-2-ol derivatives, for example 1-t-butylamino-3-(o-N-methylcarbamoylmethoxyphenoxy)propane-2-ol, processes for their manufacture and pharmaceutical compositions containing them. The compounds possess β-adrenergic blocking activity and are useful in the treatment of heart diseases and other conditions in man.

2 Claims, No Drawings

METHOD FOR PRODUCING β-ADRENERGIC BLOCKAGE WITH ALKANOLAMINE DERIVATIVES

This is a continuation, of application Ser. No. 145,897, filed May 21, 1971 now abandoned.

This invention relates to new alkanolamine derivatives which possess β-adrenergic blocking activity as demonstrated by the inhibition of isoprenaline-induced tachycardia in cats, and which are therefore useful in the treatment or prophylaxis of heart diseases, for example angina pectoris and cardiac arrhythmias, and in the treatment of hypertension and phaeochromocytoma, in man.

According to the invention there are provided new alkanolamine derivatives which possess β-adrenergic blocking activity and which have the formula:

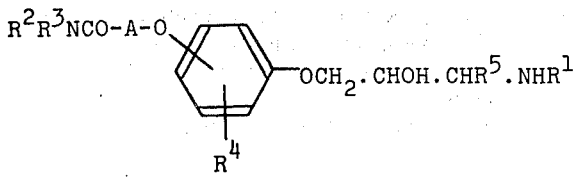

wherein $R^1$ stands for hydrogen, or for an alkyl radical which may optionally be substituted by one or more substituents selected from hydroxy, aryl and aryloxy radicals, or for a cycloalkyl or alkenyl radical; wherein $R^2$ stands for hydrogen or for an alkyl radical and $R^3$ stands for hydrogen or for an alkyl, hydroxyalkyl, alkoxyalkyl, cycloalkyl, alkenyl or aralkyl radical, or wherein $R^2$ and $R^3$, together with the adjacent nitrogen atom, form a heterocyclic ring; wherein $R^4$ stands for hydrogen or for a halogen atom or for an alkyl, alkenyl, hydroxy, alkylthio, alkoxy, alkenyloxy, aralkoxy or halogenoalkyl radical; wherein $R^5$ stands for hydrogen or for an alkyl radical; and wherein A stands for an alkylene radical; and the esters thereof; and the aldehyde-condensation products thereof; and the acid-addition salts thereof.

It is to be understood that the alkanolamine derivatives of the invention possess at least one asymmetric carbon atom, namely the carbon atom of the —CHOH— group in the alkanolamine side-chain, and they may therefore be resolved into optically-active enantiomorphic forms. At least one, and possibly both, of these enantiomorphic forms will possess β-adrenergic blocking activity. It is to be understood, therefore, that this invention encompasses the racemic form of the alkanolamine derivatives and any enantiomorphic form which possesses β-adrenergic blocking activity. It is to be understood that β-adrenergic blocking activity usually predominates in that enantiomorphic form whic has the "S" absolute configuration of the said —CHOH— group.

A suitable value for $R^1$ when it stands for an alkyl radical which may optionally be substituted is, for example, an alkyl radical of up to 6 carbon atoms, for example the methyl, ethyl, n-propyl, isopropyl, n-butyl, s-butyl, t-butyl or n-hexyl radical, which may optionally be substituted by one or more, and preferably one, hydroxy, phenyl or phenoxy radicals. The phenyl or phenoxy radical may itself bear one or more halogen, lower alkyl or lower alkoxy substituents. Preferably the alkyl or substituted alkyl radical $R^1$ contains 3 or 4 carbon atoms and is branched at the α-carbon atom. A specific value for $R^1$ when it stands for a substituted alkyl radical is, for example, the 2-hydroxyl-1-methylethyl, 2-hydroxy-1,1-dimethylethyl, 1-methyl-2-phenoxyethyl, 1,1-dimethyl-2-phenylethyl, 1-methyl-3-phenylpropyl or 2-(3,4-dimethoxyphenyl)ethyl radical.

A suitable value for $R^1$ or $R^3$ when it stands for a cycloalkyl radical is, for example, a cycloalkyl radical of up to 6 carbon atoms, for example the cyclopropyl, cyclobutyl, cyclopentyl or cyclohexyl radical.

A suitable value for $R^1$, $R^3$ or $R^4$ when it stands for an alkenyl radical is, for example, an alkenyl radical of up to 6 carbon atoms, for example the allyl radical.

A suitable value for $R^2$, $R^4$ or $R^5$ when it stands for an alkyl radical is, for example, an alkyl radical of up to 6 carbon atoms, for example the methyl, ethyl or n-propyl radical.

A suitable value for $R^3$ when it stands for an alkyl, hydroxyalkyl or alkoxyalkyl radical is, for example, an alkyl, hydroxyalkyl or alkoxyalkyl radical each of up to 10 carbon atoms, for example the methyl, ethyl, n-propyl, isopropyl, n-butyl, s-butyl, t-butyl, n-pentyl, isopentyl, n-hexyl, isohexyl, n-heptyl, n-nonyl, 2-hydroxyethyl, 2-hydroxy-1-methylethyl, 2-hydroxy-1,1-dimethylethyl or 2-methoxyethyl radical.

A suitable value for $R^3$ when it stands for an aralkyl radical is, for example, an aralkyl radical of up to 12 carbon atoms, for example the benzyl phenethyl or 1,1-dimethyl-2-phenylethyl radical.

A suitable value for the heterocyclic ring formed by $R^2$, $R^3$ and the adjacent nitrogen atom is, for example, a fully-saturated 5- or 6-membered ring, for example the pyrrolidino, piperidino or morpholino ring.

A suitable value for $R^4$ when it stands for a halogen atom is, for example, the fluorine, chlorine, bromine or iodine atom.

A suitable value for $R^4$ when it stands for an alkylthio, alkoxy or alkenyloxy radical is, for example, an alkylthio, alkoxy or alkenyloxy radical each of up to 6 carbon atoms, for example the methylthio, methoxy, isopropoxy or allyloxy radical.

A suitable value for $R^4$ when it stands for an aralkoxy radical is, for example, an aralkoxy radical of up to 10 carbon atoms, for example the benzyloxy radical.

A suitable value for $R^4$ when it stands for a halogenoalkyl radical is, for example, a halogenoalkyl radical of up to 6 carbon atoms, for example the trifluoromethyl radical.

A suitable value for A is, for example, a straightor branched-chain alkylene radical of up to 4 carbon atoms, for example the methylene, ethylene, trimethylene or ethylidene

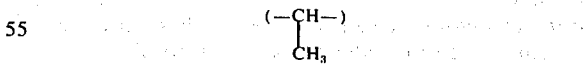

radical.

Suitable esters of the alkanolamine derivatives of the invention are, for example, esters derived from an aliphatic carboyxlic acid of up to 20 carbon atoms, for example acetic, palmitic, stearic or oleic acid, or esters derived from an aromatic carboxylic acid of up to 10 carbon atoms, for example benzoic acid, and the acid-addition salts thereof.

Suitable aldehyde condensation products of the alkanolamine derivatives of the invention are, for example, the 5-aryloxymethyl-3-substituted-oxazolidine derivatives obtained by the condensation of an aldehyde of the formula R⁶.CHO, wherein R⁶ stands for hydrogen or for an alkyl or aryl radical, with the alkanolamine derivatives of the invention, and the acid-addition salts thereof.

A suitable value for R⁶ when it stands for an alkyl radical is, for example, an alkyl radical of up to 4 carbon atoms, for example the isopropyl radical.

A suitable value for R⁶ when its stands for an aryl radical is, for example, an aryl radical of up to 10 carbon atoms, for example the phenyl radical.

Suitable acid-addition salts of the alkanolamine derivatives of the invention, or of the esters or the oxazolidines derived therefrom, are, for example, salts derived from inorganic acids, for example hydrochlorides, hydrobromides, phosphates or sulphates, or salts derived from organic acids, for example oxalates, lactates, tartrates, acetates, salicylates, citrates, benzoates, β-naphthoates, adipates or 1,1-methylenebis-(2-hydroxy-3-naphthoates), or salts derived from acidic synthetic resins, for example sulphonated polystyrene resins, for example "Zeo-Karb" 225 ("Zeo-Karb" is a Trade Mark).

One group of alkanolamine derivatives of the invention comprises compounds of the formula:

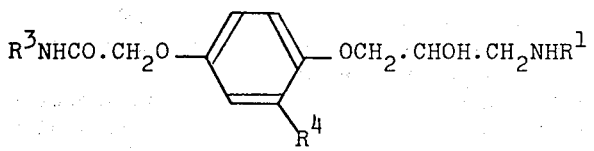

wherein R¹, R³ and R⁴ have the meanings stated above, and the acid-addition salts thereof. Of these, preferred compounds are those wherein R¹ stands for the isopropyl or t-butyl radical, R³ stands for hydrogen or for an alkyl, alkenyl or cycloalkyl radical each of up to 6 carbon atoms and R⁴ stands for hydrogen or for an alkyl, alkenyl or alkoxy radical each of up to 6 carbon atoms.

A second, and particularly preferred, group of alkanolamine derivatives of the invention comprises compounds of the formula:

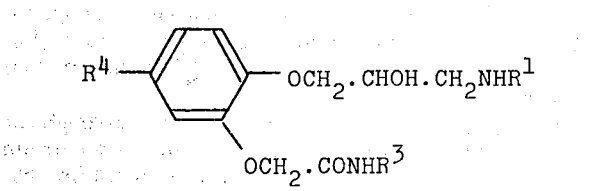

wherein R¹, R³ and R⁴ have the meanings stated above, and the acid-addition salts thereof. Of these, preferred compounds are those wherein R¹ stands for the isopropyl, t-butyl or 2-hydroxy-1,1-dimethylethyl radical, R³ stands for hydrogen or for an alkyl, alkenyl or cycloalkyl radical each of up to 6 carbon atoms and R⁴ stands for hydrogen or for the hydroxy radical or for an alkyl radical of up to 6 carbon atoms, and especially preferred compounds are those wherein R³ stands for hydrogen or for the methyl, ethyl or allyl radical and R⁴ stands for hydrogen.

Specific alkanolamine derivatives of the invention are, for example, those compounds hereinafter particularly described in Examples 1 to 29. Of these, particularly preferred compounds with respect to their high biological activity are 1-isopropylamino-3-(o-carbamoylmethoxyphenoxy)-propan-2-ol; 1-isopropylamino-3-(o-N-methylcarbamoylmethoxyphenoxy)propan-2-ol; 1-t-butylamino-3-(o-carbamoylmethoxyphenoxy)propan-2-ol; 1-t-butylamino-3-(o-N-methylcarbamoylmethoxyphenoxy)propan-2-ol; 1-isopropylamino-3-(o-N-allylcarbamoylmethoxyphenoxy)-propan-2-ol; 1-t-butylamino-3-(o-N-allylcarbamoylmethoxyphenoxy)propan-2-ol; 1-isopropylamino-3-(o-N-ethylcarbamoylmethoxyphenoxy)propan-2-ol; 1-t-butylamino-3-(o-N-ethylcarbamoylmethoxyphenoxy)-propan-2-ol; 1-isopropylamino-3-(o-N-propylcarbamoylmethoxyphenoxy)propan-2-ol and 1-t-butylamino-3-(o-N-propylcarbamoylmethoxyphenoxy)propan-2-ol and the acid-addition salts thereof.

The alkanolamine derivatives of the invention may be manufactured by any chemical process known to be suitable for the manufacture of analogous compounds.

According to a further feature of the invention there is provided a process for the manufacture of the alkanolamine derivatives of the invention which comprises assembling in sequence, by conventional chemical synthesis, the four radicals:

i. a phenoxy radical of the formula:

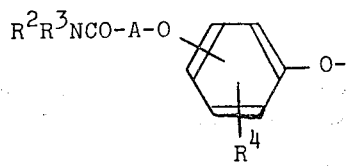

wherein R², R³, R⁴ and A have the meanings stated above;

ii. an oxygenated three-carbon radical of the formula:

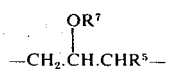

wherein R⁵ has the meaning stated above and wherein R⁷ stands for hydrogen or for a protecting group;

iii. an imino radical of the formula —NR⁸—, wherein R⁸ stands for hydrogen or for a protecting group; and iv. a radical of the formula —R¹, wherein R¹ has the meaning stated above;

whereafter if either or both of R⁷ and R⁸ stands for a protecting group, the one or two protecting groups are removed.

The various stages of the assembly may be carried out in any possible order. Thus, for example:

a. A phenol of the formula:

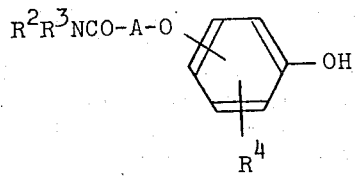

wherein R², R³, R⁴ and A have the meanings stated above, which may be obtained from the corresponding hydroxyphenoxyalkanoic acid by conventional methods of amide formation, may first be reacted with an oxygenated three-carbon derivative, for example a compound of the formula:

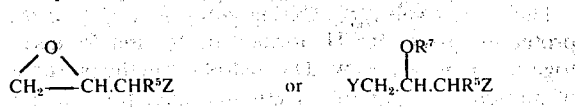

wherein $R^5$ and $R^7$ have the meanings stated above, wherein Y stands for a displaceable radical and wherein Z stands for the hydroxy radical or for a displaceable radical. If Z stands for the hydroxy radical, the intermediate compound obtained is further reacted with a reagent which will replace the primary hydroxy radical Z with a displaceable radical Y. The resulting product, which is a compound of the formula:

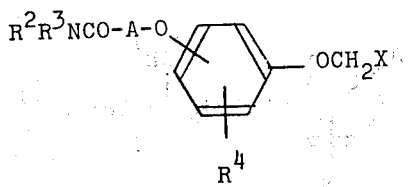

wherein $R^2$, $R^3$, $R^4$ and A have the meanings stated above and wherein X stands for the group

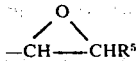

or the group

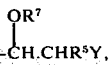

wherein $R^5$, $R^7$ and Y have the meanings stated above, or which may be, when $R^7$ stands for hydrogen, a mixture of such compounds wherein X has both meanings staged above, is then reacted with an amine of the formula $R^1R^8NH$, wherein $R^1$ and $R^8$ have the meanings stated above, or with a precursor of such an amine.

b. An oxygenated three-carbon derivative, for example a compound of the formula:

wherein $R^5$, $R^7$, Y and Z have the meanings stated above, is reacted with an amine of the formula $R^1R^8NH$, wherein $R^1$ and $R^8$ have the meanings stated above, or with a precursor of such an amine. If Z stands for the hydroxy radical the intermediate compound obtained is further reacted with a reagent which will replace the primary hydroxy radical Z with a displaceable radical Y. The resulting product, which is a compound of the formula $XCHR^5.NR^1R^8$, wherein $R^1$, $R^5$, $R^8$ and X have the meanings stated above, or which may be, when $R^7$ stands for hydrogen, a mixture of such compounds wherein X has both meanings stated above, is then reacted with a phenol of the formula:

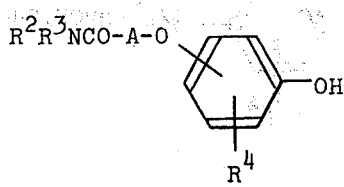

wherein $R^2$, $R^3$ and $R^4$ have the meanings stated above.

A suitable value for Y, or for Z when it stands for a displaceable radical, is, for example, a halogen atom, for example, the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

A suitable reagent which will replace the primary hydroxy radical Z with a displaceable radical Y is, for example, a halogenating agent, for example a thionyl halide, for example thionyl chloride or thionyl bromide, or a sulphonylating agent, for example and alkanesulphonyl halide or an arenesulphonyl halide, for example methanesulphonyl chloride, benzenesulphonyl chloride or toluene-p-sulphonyl chloride.

The reaction involving a phenol reactant may be carried out in the presence of an acid-binding agent, for example an alkali metal hydroxide, for example sodium hydroxide, or an organic base, for example piperidine. Alternatively, an alkali metal derivative of the phenol reactant, for example the sodium or potassium derivative, may be used as starting material. The reaction may be carried out in a diluent or solvent, for example methanol or ethanol, and it may be accelerated or completed by the application of heat, for example by heating to the boiling point of the diluent or solvent.

The reaction invilving an amine of the formula $R^1R^8NH$ may be carried out at ambient temperature or it may be accelerated or completed by the application of heat, for example by heating to a temperature of 90°–110°C.; it may be carried out at atmospheric or at an elevated pressure, for example by heating in a sealed vessel; and it may be carried out in an inert diluent or solvent, for example methanol or ethanol, or an excess of the amine of the formula $R^1R^8NH$, wherein $R^1$ and $R^8$ have the meanings stated above, may be used as diluent or solvent.

A suitable precursor of the amine of the formula $R^1R^8NH$ is, for example, a urea of the formula $R^1R^8N.CO.NR^1R^8$, wherein $R^1$ and $R^8$ have the meanings stated above. The reaction involving a urea may be carried out in a high boiling diluent or solvent, for example tetralin, decalin or benzonitrile, and it may be carried out at a temperature of between 150° and 220°C.

c. The series of reactions described under (a) or (b) above may be carried out except that an amine of the formula $R^8NH_2$ is used in place of an amine of the formula $R^1R^8NH$, it being understood that when $R^8$ stands for hydrogen the amine is ammonia. The radical $R^1$ may then be inserted as a separate step, for example either by the reaction of the final product from the series of reactions described under (a) or (b) above with a compound of the formula $R^1Y$, wherein $R^1$ and Y have the meanings stated above, or, when $R^8$ stands for hydrogen, by the reaction under reducing conditions of the final product from the series of reactions described under (a) or (b) above with a carbonyl compound of the formula $R^9.CO.R^{10}$, wherein $R^9$ stands for an alkyl radical and $R^{10}$ stands for an alkyl, aralkyl, aryloxyalkyl or hydroxyalkyl radical, or wherein $R^9$ and $R^{10}$ are joined together with the adjacent carbon atom to form a cycloalkyl radical, such that the radical —$CHR^9R^{10}$ has the same meaning as is stated above for $R^1$.

A particularly suitable compound of the formula $R^1Y$ is isopropyl bromide. The reaction involving a compound of the formula R¹Y may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or more solvents selected from water, ethanol and an excess of the carbonyl compound used as starting material.

It is to be understood that when in the starting material R⁴ stands for a halogen atom or for an alkenyl, aklylthio, alkenyloxy or aralkoxy radical, the use of hydrogen and a hydrogenation catalyst is likely to modify the substitutent R⁴, for example by replacement of a chlorine, bromine, iodine or alkylthio substituent by hydrogen, reduction of an alkenyl or alkenyloxy substituent to an alkyl or alkoxy substituent respectively, and hydrogenolysis of an α-arylalkoxy substituent to give the hydroxy substituent.

d. A compound wherein either or both of R⁷ and R⁸ stands for a protecting group may be prepared by the series of reactions described under (a) or (b) or (c) above. Alternatively, a suitable protecting group may be introduced by conventional means into an intermediate compound at any stage preceding the final stage.

A suitable value for R⁷ when it stands for a protecting group is, for example, a hydrogenolysable radical, for example α-arylalkyl, α-arylalkoxy-carbonyl or α-arylalkoxymethyl radical, for example the benzyl, benzyloxycarbonyl or benzyloxymethyl radical, or an acyl radical, for example an alkanoyl radical of up to 20 carbon atoms or an aroyl radical of up to 10 carbon atoms, or an α-alkoxyalkyl radical (an acetal radical), for example the tetrahydropyranyl radical.

A suitable value for R⁸ when it stands for a protecting group is, for example, a hydrogenolysable or acyl radical as defined for R⁷, or a carbamoyl radical, for example a radical of the formula —CONHR¹, wherein R¹ has the meaning stated above.

Alternatively, R⁷ and R⁸ may be joined together so that one protecting group serves to protect both the oxygen and nitrogen atom. Such a protecting group may be, for example, the carbonyl (—CO—) radical, such that it forms, together with the adjacent oxygen and nitrogen atoms and two carbonn atoms of the three-carbon radical, an oxazolidinone nucleus, or it may be a radical of the formula —CHR⁶—, wherein R⁶ has the meaning stated above, such that if forms, together with the adjacent oxygen and nitrogen atoms and two carbon atoms of the three-carbon radical, an oxazolidine nucleus.

The hydrogenolysable protecting group R⁷ or R⁸ may be removed for example, by catalytic hydrogenation, for example by hydrogenation in the presence of a palladium-on-charcoal catalyst, in an inert diluent or solvent, for example ethanol or aqueous ethanol. The process may be accelerated or completed by the presence of an acidic catalyst, for example hydrochloric or oxalic acid.

The acyl protecting group R⁷ or R⁸, or the carbamoyl protecting group R⁸, or the carbonyl protecting group formed by R⁷ and R⁸ taken together, may be removed by hydrolysis in the presence of a base, for example an alkali metal hydroxide, in a diluent or solvent, for example water, methanol, ethanol or a mixture thereof.

The α-alkoxyalkyl protecting group R⁷ or R⁸, or the protecting group R⁶CH— formed by R⁷ and R⁸ taken together, may be removed by hydrolysis in the presence of an acid, for example a mineral acid, for example aqueous hydrochloric acid, and the hydrolysis may be carried out at a temperature of up to 100°C.

According to a further feature of the invention there is provided a process for the manufacture of the alkanolamine derivatives of the invention which comprises elaborating by conventional chemical means the sidechain of the formula R²R³NCO-A-, wherein R², R³ and A have the meanings stated above, onto a phenoxy radical of the formula:

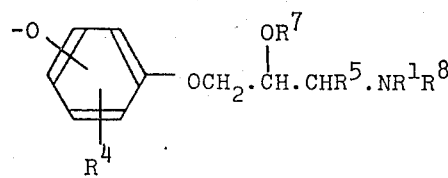

wherein R¹, R⁴, R⁵, R⁷ and R⁸ have the meanings stated above, whereafter if either or both of R⁷ and R⁸ stands for a protecting group, the one or two protecting groups are removed.

The elaboration may be carried out by the reaction of a compound of the formula:

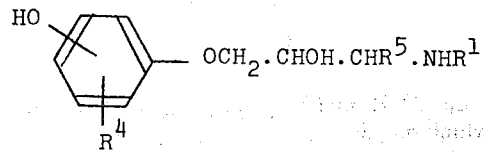

wherein R¹, R⁴ and R⁵ have the meanings stated above, or of a metal salt thereof, with a compound of the formula:
wherein R², R³, A and Y have the meanings stated above.

A suitable metal salt of the starting material is, for example, an alkali metal salt, for example the sodium salt, or the thallium salt. If a metal salt is not used, the reaction may be carried out in the presence of an acid-binding agent. The reaction may be carried out in a diluent or solvent, for example ethanol or dimethylformamide, and it may be accelerated or completed by the application of heat, for example by heating to a temperature of up to 150°C.

Alternatively, the final stage of the elaboration may be carried out by the reaction of a reactive derivative of an acid of the formula:

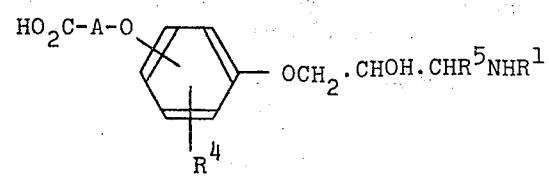

wherein $R^1$, $R^4$, $R^5$ and A have the meanings stated above, with an amine of the formula $R^2R^3NH$, wherein $R^2$ and $R^3$ have the meanings stated above.

A suitable reactive derivative of the acid is, for example, an acyl halide, for example the acyl chloride, or acyl anhydride, or an ester, for example the methyl or ethyl ester, or the acid itself in the presence of a condensing agent, for example a carbodiimide, for example N,N-dicyclohexylcarbodiimide. The process may be carried out under conditions conventionally used for the manufacture of amides.

It is to be understood that a compound wherein $R^3$ or $R^4$ stands for a functional radical may be converted into a different compound wherein $R^3$ or $R^4$ stands for a different radical. Thus, for example, a compound wherein $R^3$ stands for hydrogen may be converted into the corresponding compound wherein $R^3$ has the same meaning as $R^1$, during the course of the process of the invention described under (a) above which involves an amine of the formula $R^1NH_2$; and a compound wherein $R^4$ stands for an alkenyl, alkenyloxy or aralkoxy radical may be converted to the corresponding compound wherein $R^4$ stands for, respectively, an alkyl, alkoxy or hydroxy radical, by reaction with hydrogen in the presence of a catalyst, as already stated under (c) above.

According to a further feature of the invention there is provided a process for the manufacture of optically-active enantiomorphs of the alkanolamine derivatives of the invention which comprises the resolution by conventional means of the corresponding racemic alkanolamine derivative of the invention.

The said resolution may be carried out by reacting the racemic alkanolamine derivative with an optically-active acid, follwd by fractional crystallisation of the diastereoisomeric mixture of salts thus obtained, from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

According to a further feature of the invention there is provided a process for the manufacture of the esters of the alkanolamine derivatives of the invention which comprises the reaction of an acid-addition salt of the corresponding unesterified alkanolamine derivative with an acylating agent.

A suitable acylating agent is, for example, an acid halide or acid anhydride derived from an aliphatic carboxylic acid, for example such an acid of not more than 20 carbon atoms, or derived from an aromatic carboxylic acid, for example such an acid of not more than 10 carbon atoms. Thus a suitable acylating agent is, for example, acetic anhydride, acetyl chloride or benzoyl chloride. The acylation may be carried out in a diluent or solvent, which, in the case where an acid anhydride is used as acylating agent, may conveniently be the acid from which the anhydride is derived.

Alternatively, an ester of the invention may be obtained by carrying out the process of the invention as described under (a), (b) or (c) above wherein $R^7$ stands for a protecting group which is an acyl radical, and then not carrying out the final hydrolysis step as described under (d) above.

According to a further feature of the invention there is provided a process for the manufacture of the aldehydecondensation products (oxazolidine derivatives) of the invention which have the formula:

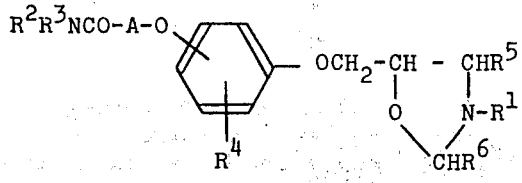

wherein $R^1$, $R^2$, $R^3$, $R^4$, $R^5$, $R^6$ and A have the meanings stated above, which comprises assembling by conventional chemical synthesis, in the appropriate relationship, the four radicals: i. a phenoxy radical of the formula:

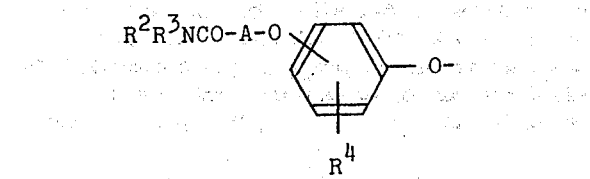

wherein $R^2$, $R^3$, $R^4$ and A have the meanings stated above; ii. an oxygenated three-carbon radical of the formula:

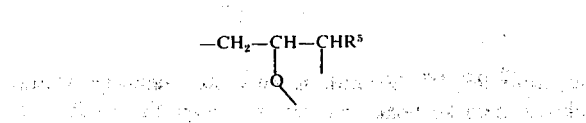

wherein $R^5$ has the meaning stated above; iii. an imino radical of the formula

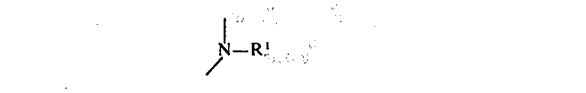

wherein $R^1$ has the meaning stated above; and iv. a radical of the formula

wherein $R^6$ has the meaning stated above.

The various stages of the assembly may be carried out in any possible order. Thus, for example: a. The alkanolamine derivative of the invention, or an acid-addition salt thereof, may be reacted with an aldehyde of the formula $R^6.CHO$, wherein $R^6$ has the meaning stated above.

The said reaction may be carried out in a diluent or solvent, for example ethanol, optionally in the presence of a catalyst, for example hydrochloric acid, acetic acid or iodine, and it may be accelerated or completed by the application of heat. The water formed during the reaction may optionally be removed by azeotropic distillation using a suitable solvent, for example benzene, toluene or chloroform, as entraining agent, or it may optionally be removed by means of a dehydrating agent, for example anhydrous potassium carbonate. (b) An epoxide of the formula:

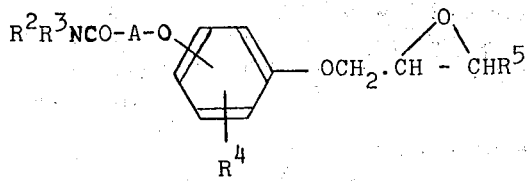

wherein $R^2$, $R^3$, $R^4$, $R^5$ and A have the meanings stated above, may be reacted with a Schiff base of the formula $R^1N=CHR^6$, wherein $R^1$ and $R^6$ have the meanings stated above.

The said reaction may be carried out in the presence of a Lewis acid, for example stannic chloride, boron trifluoride or zinc chloride, and it may be carried out in a diluent or solvent, for example carbon tetrachloride, at a low temperature, for example at a temperature of between 10° and 20°C. The Schiff base used as starting material may be obtained by the reaction of an amine of the formula $R^1NH_2$, wherein $R^1$ has the meaning stated above, with an aldehyde of the formula $R^6CHO$, wherein $R^6$ has the meaning stated above. (c) A phenol of the formula:

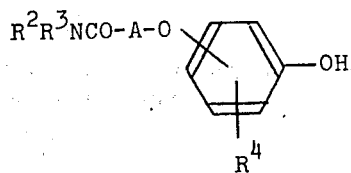

wherein $R^2$, $R^3$, $R^4$ and A have the meanings stated above, may be reacted with an oxazolidine of the formula:

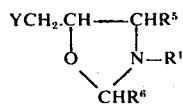

wherein $R^1$, $R^5$, $R^6$ and Y have the meanings stated above.

The said reaction may be carried out in a diluent or solvent, for example methanol, at an elevated temperature, for example at the boiling point of the diluent or solvent, and it may be carried out in the presence of a base, for example an alkali metal hydroxide, for example sodium hydroxide. The oxazolidine starting material may be obtained by the reaction of a compound of the formula:

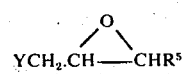

wherein $R^5$ and Y have the meanings stated above, for example epichlorohydrin, with a Schiff base of the formula $R^1N=CHR^6$, wherein $R^1$ and $R^6$ have the meanings stated above, in the presence of a Lewis acid.

The alkanolamine derivatives of the invention and the esters and aldehyde-condensation products thereof in free base form may be converted into acid-addition salts thereof by interaction with an acid by conventional means.

As stated above, the alkanolamine derivatives of the invention and the esters, aldehyde-condensation products and acid-addition salts thereof are of value in the treatment or prophylaxis of heart diseases. Furthermore, some of these compounds possess selective β-adrenergic blocking activity. Compounds exhibiting this selective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine [for example isoprenaline, that is, 1-(3,4-dihydroxyphenyl)-2-isopropylaminoethanol] but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the selective compound will substantially inhibit the unwanted stimulatory effects of the bronchodilator on the heart but will not hinder the desirable therapeutic effect of the bronchodilator.

Many compounds possessing β-adrenergic blocking activity are known, many of these being 1-aryloxy-3-amino-2-propanol derivatives, and it is also known that some of these compounds, especially those wherein the 1-aryloxy radical bears an acylamino substituent, possess selective β-adrenergic blocking activity. It is a desirable, although not essential, feature of a β-adrenergic blocking agent which is to be used clinically that the agent does not possess any substantial amount of intrinsic sympathomimetic activity. The compound with which most clinical experience has been obtained, propranolol [1-isopropylamino-3-(naphth-1-yloxy)-2-propanol, which is described and claimed in United Kingdom Patent Specification No. 994,918], is totally devoid of intrinsic sympathomimetic activity. However, no compound which possesses selective β-adrenergic blocking activity as defined above is known which is devoid of intrinsic sympathomimetic activity. In particular, the selective β-adrenergic blocking agent with which most clinical experience has been obtained, practolol [1-(4-acetamidophenoxy)-3-isopropylamino-2-propanol, which is described and claimed in United Kingdom Patent Specification No. 1,078,852], possesses significant intrinsic sympathomimetic activity.

It has now been found that some of the compounds of the present invention, and especially the compounds 1-(2-allyl-4-carbamoylmethoxyphenoxy)-3-isopropylamino-2-propanol and 1-(4-carbamoylmethoxy-2-n-propylphenoxy)-3-isopropylamino-2-propanol, possess selective β-adrenergic blocking activity as determined by the inhibition of isoprenaline-induced tachycardia in cats, and by freedom from antagonism of isoprenaline-induced vasodilatation in cats or of the relief produced by isoprenaline of histamine-induced bronchospasm in guinea-pigs. These compounds are, however, devoid of intrinsic sympathomimetic activity as demonstrated by their failure to increase the heart rate of rats from which natural catecholamines have been depleted by pre-treatment with syrosingopine.

According to a further feature of the invention, therefore, there are provided pharmaceutical compositions comprising an active ingredient one or more alkanolamine derivatives of the invention, or esters thereof, or aldehyde condensation products thereof, or acid-addition salts thereof, in association with a pharmaceutically-acceptable diluent or carrier therefor.

As suitable compositions there may be mentioned, for example, tablets, capsules, aqueous or oily solutions or suspensions, emulsions, injectable aqueous or oily solutions or suspensions, dispersible powders, sprays and aerosol formulations.

The pharmaceutical compositions of the invention may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; myocardial depressants, for example quinidine; agents used in the treatment of Parkinson's disease, for example benzhexol; cardiotonic agents, for example digitalis preparations; and sympathomimetic bronchodilators, for example isoprenaline, orciprenaline, adrenaline and ephedrine.

It is expected that the alkanolamine derivative would be given to man at a total oral dose of between 25 mg. and 1200 mg. daily, at doses spaced at 6–8 hourly intervals, or at an intravenous dose of between 1 mg. and 25 mg. Preferred oral dosage forms are tablets or capsules containing between 25 and 200 mg., and preferably 50 mg. or 100 mg., of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.2% w/v of active ingredient.

The invention is illustrated but not limited by the following Examples:

EXAMPLE 1

A solution of 2 g. of 1-chloro-3-(p-carbamoylmethoxyphenoxy)propan-2-ol and 15 ml. of isopropylamine in 15 ml. of methanol is heated in a sealed tube at 110°C. for 12 hours. The mixture is evaporated in dryness and the residue is partitioned between 40 ml. of chloroform and 40 ml. of aqueous 2N-hydrochloric acid. The aqueous acidic layer is separated, made alkaline with sodium carbonate and extracted twice with 40 ml. of chloroform each time. The combined extracts are dried and evaporated to dryness and the residue is crystalised from ethyl acetate. There is thus obtained 1-isopropylamino-3-(p-N-isopropylcarbamoylmethoxyphenoxy)propan-2-ol, m.p. 108°–109°C.

The 1-chloro-3-(p-carbamoylmethoxyphenoxy)propan-2-ol used as starting material may be obtained as follows:

A mixture of 1.5 g. of p-hydroxyphenoxyacetamide, 15 ml. of epichlorohydrin and 6 drops of piperidine is heated at 95°–100°C. for 6 hours and then evaporated to dryness. The residual oil consists of 1-chloro-3-(p-carbamoylmethoxyphenoxy)propan-2-ol and is used without further purification.

The process described above is repeated except that o-hydroxyphenoxyacetamide is used as starting material in place of p-hydroxyphenoxyacetamide. There is thus obtained 1-isopropylamino-3-(o-N-isopropylcarbamoylmethoxyphenoxy)propan-2-ol, m.p. 89°–94°C. (crystallised from a mixture of benzene and petroleum ether b.p. 60°–80°C.).

EXAMPLE 2

A mixture of 1.5 g. of 1,2-epoxy-3(p-carbamoylmethoxyphenoxy)propane and 50 ml. of isopropylamine is allowed to stand at room temperature for 72 hours. The mixture is evaporated to dryness and the residue is crystallised from ethyl acetate. There is thus obtained 1-isopropylamino-3-(p-carbamoylmethoxyphenoxy)-propan-2-ol, m.p. 123°–125°C.

The 1,2-epoxy-3-(p-carbamoylmethoxyphenoxy)propane used as starting material may be obtained as follows:

A mixture of 1.5 g. of 1-chloro-3-(p-carbamoylmethoxyphenoxy)propan-2-ol and 25 ml. of aqueous N-sodium hydroxide solution is shaken at room temperature for 1 hour and is then extracted twice with 40 ml. of chloroform each time. The combined chloroform extracts are washed with water, dried and then evaporated to dryness. The residue consists of 1,2-epoxy-3-(p-carbamoylmethoxyphenoxy)propane and is used without further purification.

EXAMPLE 3

A solution of 1 g. of 1-(2-allyl-4-carbamoylmethoxyphenoxy)-3-chloropropan-2-ol and 20 ml. of isopropylamine in 10 ml. of methanol is heated in a sealed tube at 110°C. for 12 hours. The mixture is evaporated to dryness and the residue is partitioned between 40 ml. of chloroform and 40 ml. of aqueous 2N-hydrochloric acid. The aqueous acidic layer is separated, made alkaline with sodium carbonate and extracted twice with 40 ml. of chloroform each time. The combined extracts are dried and evaporated to dryness and the residue is crystallized from ethyl acetate. There is thus obtained 1-(2-allyl-4-carbamoylmethoxyphenoxy)-3-isopropylaminopropan-2-ol, m.p. 121°–123°C.

The 1-(2-allyl-4-carbamoylmethoxyphenoxy)-3-chloropropan-2-ol used as starting material may be obtained as follows:

A mixture of 7.7 g. of p-hydroxyphenoxyacetamide, 3.95 ml. of allyl bromide, 12.7 g. of anhydrous potassium carbonate, 200 ml. of acetone and a trace of potassium iodide is stirred and heated under reflux for 24 hours. 200 Ml. of water are then added and the acetone is removed by evaporation under reduced pressure. The suspension is extracted twice with 200 ml. of chloroform each time, and the combined chloroform extracts are dried and evaporated to dryness. The residue consists of p-allyloxyphenoxyacetamide and is used without further purification.

A solution of 8 g. of p-allyloxyphenoxyacetamide in 100 ml. of diphenyl ether is heated under reflux for 10 minutes. The mixture is cooled, 250 ml. of chloroform are added and the mixture is extracted twice with 100 ml. of aqueous 2N-sodium hydroxide solution each time. The combined extracts are acidified and the resulting suspension is extracted twice with 100 ml. of ethyl acetate each time. The combined ethyl acetate extracts are dried and evaporated to dryness and the residue is crystallised from benzene. There is thus obtained 3-allyl-4-hydroxyphenoxyacetic acid, m.p. 100°–102°C.

A solution of 3.2 g. of 3-allyl-4-hydroxyphenoxyacetic acid in 70 ml. of ethanol containing 10 drops of sulphuric acid is heated under reflux for 4 hours. The solution is evaporated to half its original volume and poured into 250 ml. of water. The suspension is extracted twice with 100 ml. of ethyl acetate each time, and the combined ethyl acetate extracts are washed successively with dilute aqueous sodium bicarbonate solution, and water, and then dried and evaporated to dryness. There is thus obtained as residue ethyl 3-allyl-4-hydroxyphenoxyacetate which is used without further purification.

A mixture of 2.5 g. of ethyl 3-allyl-4-hydroxyphenoxyacetate and 150 ml. of aqueous ammonium hydroxide solution (specific gravity 0.880) is stirred for 24 hours and is then evaporated to dryness. The residue is crystallised from chloroform and there is thus obtained 3-allyl-4-hydroxyphenoxyacetamide, m.p. 84°–87°C.

A mixture of 1 g. of 3-allyl-4-hydroxyphenoxyacetamide, 10 ml. of epichlorohydrin and 3 drops of piperidine is heated at 95°–100°C. for 6 hours and is then evaporated to dryness. The residual oil consists of 1-(2-allyl-4-carbamoylmethoxyphenoxy)-3-chloropropan-2-ol and is used without further purification.

EXAMPLE 4

0.1 G. of platinum oxide catalyst is added to a solution of 0.4 g. of 1-(2-allyl-4-carbamoylmethoxyphenoxy)-3-isopropylaminopropan-2-ol in 50 ml. of ethanol and the mixture is shaken in an atmosphere of hydrogen at room temperature and atmospheric pressure until one molecular proportion of hydrogen is absorbed. The mixture is filtered, the filtrate is evaporated to dryness and the residue is crystallised from ethyl acetate. There is thus obtained 1-(4-carbamoylmethoxy-2-n-propylphenoxy)-3-isopropylamino-propan-2-ol, m.p. 141°–143°C.

EXAMPLE 5

A solution of 1 g. of 1-chloro-3-(p-N-methylcarbamoylmethoxyphenoxy)propan-2-ol and 20 ml. of isopropylamine in 10 ml. of methanol is heated in a sealed tube at 110°C. for 12 hours. The mixture is evaporated to dryness and the residue is partitioned between 40 ml. of chloroform and 40 ml. of aqueous 2N-hydrochloric acid. The aqueous acidic layer is separated, made alkaline with sodium carbonate and extracted twice with 40 ml. of chloroform each time. The combined extracts are dried and evaporated to dryness and the residue is crystallised from ethyl acetate. There is thus obtained 1-isopropylamino-3-(p-N-methylcarbamoylmethoxyphenoxy)propan-2-ol, m.p. 129–131°C.

The 1-chloro-3-(p-N-methylcarbamoylmethoxyphenoxy)-propan-2-ol used as starting material may be obtained as follows:

A mixture of 3 g. of methyl p-hydroxyphenoxyacetate and 100 ml. of 30% w/v aqueous monomethylamine solution is stirred for 24 hours and then evaporated to dryness. The residue is crystallised from water and there is thus obtained p-hydroxyphenoxy-N-methylacetamide, m.p. 124°–126°C.

A mixture of 1 g. of p-hydroxyphenoxy-N-methylacetamide, 10 ml. of epichlorohydrin and 3 drops of piperidine is heated at 95°–100°C. for 6 hours and then evaporated to dryness. The residue consists of 1-chloro-3-(p-N-methylcarbamoylmethoxyphenoxy)-propan-2-ol and is used without any further purification.

EXAMPLE 6

The process described in Example 5 is repeated except that the appropriate 1-chloro-3-(p-N-substituted-carbamoylmethoxyphenoxy)propan-2-ol derivative and either isopropylamine of t-butylamine are used as starting materials. There are thus obtained the compounds described in the following table:

$R^2NHCO.CH_2O$—⟨benzene⟩—$OCH_2.CHOH.CH_2NHR^1$

| R[1] | R[2] | m.p. (°C.) | crystallisation solvent |
|---|---|---|---|
| isopropyl | n-butyl | 75–78 | cyclohexane |
| isopropyl | allyl | 112–114 | ethyl acetate |
| isopropyl | cyclopentyl | 101–103 | ethyl acetate/ petroleum ether (b.p. 60–80°C.) |
| isopropyl | cyclohexyl | 111–114 | ethyl acetate |
| isopropyl | s-butyl | 98–100 | ethyl acetate |
| isopropyl | t-butyl | 90–92 | cyclohexane |
| isopropyl | isohexyl | 80–83 | toluene |
| isopropyl | n-hexyl | 92–94 | cyclohexane |
| t-butyl | allyl | 78–80 | benzene/petroleum ether (b.p. 60–80°C.) |

The 1-chloro-3-(p-N-substituted-carbamoylmethoxyphenoxy)propan-2-ol derivatives used as starting material may be obtained by reacting p-hydroxyphenoxyacetic acid successively with acetyl chloride, thionyl chloride, the amine of the formula $R^2NH_2$ in benzene solution, aqueous sodium hydroxide solution at room temperature (to hydrolyse the O-acetyl derivative) and finally epichlorohydrin in the presence of piperidine.

EXAMPLE 7

A solution of 1 g. of 1-(4-carbamoylmethoxy-2-methoxyphenoxy)-3-chloropropan-2-ol and 20 ml. of isopropylamine in 10 ml. of methanol is heated in a sealed tube at 110°C. for 12 hours. The mixture is evaporated to dryness and the residue is partitioned between 40 ml. of chloroform and 40 ml. of aqueous 2N-hydrochloric acid. The aqueous acidic layer is separated, made alkaline with sodium carbonate and extracted twice with 40 ml. of chloroform each time. The combined extracts are dried and evaporated to dryness and the residue is crystallised from ethyl acetate. There is thus obtained 1-(4-carbamoylmethoxy-2-methoxyphenoxy)-3-isopropylaminopropan-2-ol, m.p. 125°–128°C.

The 1-(4-carbamoylmethoxy-2-methoxyphenoxy)-3-chloropropan-2-ol used as starting material may be obtained as follows:

A mixture of a solution of 9.4 g. of 4-benzyloxy-3-methoxyphenol in 160 ml. of 1% w/v aqueous sodium hydroxide solution and a solution of 7.7 g. of chloroacetic acid in 80 ml. of 8% w/v aqueous sodium hydroxide solution is heated at 95°–100°C. for 8 hours. The mixture is cooled, washed with 100 ml. of ether, acidified with concentrated aqueous hydrochloric acid and extracted twice with 100 ml. of ethyl acetate each time. The combined ethyl acetate extracts are shaken twice with 100 ml. of dilute aqueous sodium bicarbonate solution each time and the combined sodium bicarbonate extracts are acidified with concentrated aqueous hydrochloric acid and extracted twice with 100 ml. of ethyl acetate each time. The combined ethyl acetate extracts are dried and evaporated to dryness and the residue is crystallized from benzene. There is thus obtained 4-benzyloxy-3-methoxyphenoxyacetic acid, m.p. 94°–97°C.

1.0 G. of a 5% palladium-on-charcoal catalyst is added to a solution of 7.5 g. of 4-benzyloxy-3-methoxyphenoxyacetic acid in 250 ml. of ethanol and the mixture is shaken in an atmosphere of hydrogen at room temperature and atmospheric pressure until one molecular proportion of hydrogen is absorbed. The mixture is filtered and the filtrate is evaporated to dryness. The residue is crystallised from ethyl acetate and there is thus obtained 4-hydroxy-3-methoxyphenoxyacetic acid, m.p. 152°–155°C.

A solution of 1.5 g. of 4-hydroxy-3-methoxyphenoxyacetic acid in 40 ml. of methanol containing 6 drops of sulphuric acid is heated under reflux for 4 hours. The solution is evaporated to half its original volume and poured into 150 ml. of water. The suspension is extracted twice with 75 ml. of ethyl acetate each time and the combined extracts are washed successively with dilute aqueous sodium bicarbonate solution and water, and then dried and evaporated to dryness. There is thus obtained methyl (4-hydroxy-3-methoxyphenoxy)acetate which is used without further purification.

A mixture of 1.5 g. of methyl (4-hydroxy-3-methoxyphenoxy)acetate and 40 ml. of aqueous ammonium hydroxide solution (specific gravity 0.880) is stirred at room temperature for 24 hours and then evaporated to dryness. The residue is crystallised from water and there is thus obtained 4-hydroxy-3-methoxyphenoxyacetamide, m.p. 126°–128°C.

A mixture of 1 g. of 4-hydroxy-3-methoxyphenoxyacetamide, 10 ml. of epichlorohydrin and 3 drops of piperidine is heated at 95°–100°C. for 6 hours and then evaporated to dryness. The residual oil consists of 1-(4-carbamoylmethoxy-2-methoxyphenoxy)-3-chloropropan-2-ol and is used without further purification.

EXAMPLE 8

A mixture of 3.9 g. of 1-(o-N-methylcarbamoylmethoxyphenoxy)-2,3-epoxypropane and 30 ml. of isopropylamine is heated at 95°–100°C. for 6 hours. The mixture is evaporated to dryness and the residue is partitioned between 50 ml. of chloroform and 50 ml. of aqueous 2N-hydrochloric acid. The aqueous acidic acid is separated, made alkaline with solid sodium carbonate and extracted three times with 50 ml. of chloroform each time. The combined extracts are dried and evaporated to dryness under reduced pressure and the residue is crystallised from ethyl acetate. There are thus obtained 2.8 g. of 1-isopropylamine-3(o-N-methylcarbamoylmethoxyphenoxy)propan-2-ol, m.p. 117°C.

The 1-(o-N-methylcarbamoylmethoxyphenoxy)-2,3-epoxypropane used as starting material may be obtained as follows:

3 G. of 1,4-benzodioxan-2-one are added portionwise to a stirred, ice-cold, 27% w/v aqueous solution of methylamine, the temperature of the mixture being kept below 10°C., and after addition is complete the mixture is stirred at room temperature for a further 2 hours. The solution is evaporated to dryness under reduced pressure and the residue is crystallised from water. There is thus obtained o-hydroxyphenoxy-N-methylacetamide, m.p. 149°–150°C.

The o-hydroxyphenoxy-N-methylacetamide is dissolved in a solution of 0.6 g. of sodium hydroxide in 20 ml. of water, 20 ml. of epichlorohydrin are added and the mixture is stirred at room temperature for 17 hours. 20 Ml. of chloroform are then added and the organic layer is separated, washed with water and evaporated to dryness. There is thus obtained 1-(o-N-methylcarbamoylmethoxyphenoxy)-2,3-epoxypropane as an oil which is used without further purification.

EXAMPLE 9

The process described in Example 8 is repeated except that the appropriate 1-(o-carbamoylmethoxyphenoxy)-2,3-epoxypropane is used in place of 1-(o-N-methylcarbamoylmethoxyphenoxy)-2,3-epoxypropane, and there are thus obtained the compounds described in the following table:

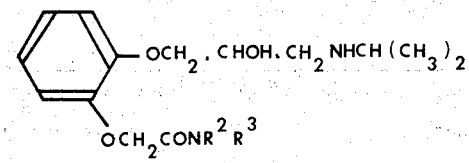

| $R^2$ | $R^3$ | m.p. (°C.) | crystallisation solvent |
|---|---|---|---|
| H | H | 108–109 | benzene/petroleum ether (b.p. 60–80°C.) |
| H | ethyl | 97–98 | benzene/petroleum ether (b.p. 60–80°C.) |
| H | n-butyl | 83–84 | ethyl acetate/petroleum ether (b.p. 60–80°C.) |
| H | cyclopentyl | 72–74 | benzene/petroleum ether (b.p. 60–80°C.) |
| H | cyclohexyl | 92–94 | benzene |
| H | allyl | 86 | benzene/petroleum ether (b.p. 60–80°C.) |
| H | benzyl | 84–86 | benzene/petroleum ether (b.p. 60–80°C.) |
| ethyl | ethyl | 55–58 | benzene/petroleum ether (b.p. 60–80°C.) |
| pentamethylene | | hydrogen oxalate 98–100 | acetone |

The 1-(o-carbamoylmethoxyphenoxy)-2,3-epoxypropane derivatives used as starting materials may be obtained from the corresponding phenol and epichlorohydrin by a similar process to that described in the last paragraph of Example 8. The phenols are themselves novel compounds, and these may be obtained by a similar process to that described in the second part of Example 8 from 1,4-benzodioxan-2-one and the appropriate amine. The novel phenols are characterised by the melting points shown in the following table:

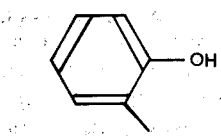

| $R^2$ | $R^3$ | m.p. (°C.) |
|---|---|---|
| H | H | 128–129 |
| H | ethyl | 138–139 |
| H | n-butyl | 96–98 |
| H | cyclopentyl | 97–98 |
| H | cyclohexyl | 110–112 |
| H | allyl | 99–100 |
| H | benzyl | 145 |
| ethyl | ethyl | 66–68 |
| pentamethylene | | 93–95 |

EXAMPLE 10

The process described in Example 8 is repeated except that the appropriate amine is used in place of isopropylamine. There are thus obtained the compounds described in the following table:

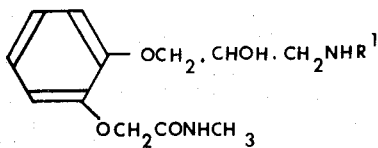

| R¹ | m.p. (°C.) | crystallisation solvent |
|---|---|---|
| H | 88–90* | benzene/petroleum ether (b.p. 60–80°C.) |
| methyl | 97–100* | ethyl acetate/petroleum ether (b.p. 60–80°C.) |
| s-butyl | 98–100 | benzene/petroleum ether (b.p. 60–80°C.) |
| t-butyl | 96–97 | benzene/petroleum ether (b.p. 60–80°C.) |
| n-hexyl | 87 | ethyl acetate |
| allyl | 92–93 | benzene |
| 2-hydroxy-1,1-dimethylethyl | 98–101 | benzene/petroleum ether (b.p. 60–80°C.) |
| 2-(3,4-dimethoxyphenoxy)ethyl | oil** | — |

*An aqueous solution of ammonia or methylamine is used and the reaction is carried out at room temperature.
**A solution of 2-(3,4-dimethoxyphenyl)ethylamine in methanol is used and the reaction is carried out at reflux temperature.

The process described above is repeated except that the appropriate amine and the appropriate 1-(o-carbamoylmethoxyphenoxy)-2,3-epoxypropane are used as starting materials, and there are thus obtained: 1-t-butylamino-3-(o-carbamoylmethoxyphenoxy)propan-2-ol; 1-t-butylamino-3-(o-N-allylcarbamoylmethoxyphenoxy)propan-2-ol; and 1-(2-hydroxy-1,1-dimethylethylamino)-3-(o-N-allylcarbamoylmethoxyphenoxy)propan-2-ol, all of which are oils from which no crystalline derivative has been obtained.

EXAMPLE 11

The process described in Example 8 is repeated except that 1-(4-bromo-2-N-methylcarbamoylmethoxyphenoxy)-2,3-epoxypropane is used as starting material in place of 1-(o-N-methylcarbamoylmethoxyphenoxy)-2,3-epoxypropane. There is thus obtained 1-isopropylamino-3-(4-bromo-2-N-methylcarbamoylmethoxyphenoxy)propan-2-ol, m.p. 130°–132°C. (crystallised from ethyl acetate).

The 1-(4-bromo-2-N-methylcarbamoylmethoxyphenoxy)-2,3-epoxypropane used as starting material may be obtained as follows:

A solution of 0.55 ml. of bromine in 10 ml. of glacial acetic acid is added to a stirred, ice-cooled, fine suspension of 1.7 g. of o-hydroxyphenoxyacetic acid in 25 ml. of glacial acetic acid, and the mixture is stirred at room temperature for 20 hours and then poured into 300 ml. of water. The aqueous suspension is extracted three times with 200 ml. of chloroform each time and the combined chloroform extracts are dried and evaporated to dryness under reduced pressure. The residue is crystallised from water and there is thus obtained 5-bromo-2-hydroxyphenoxyacetic acid, m.p. 1602°–162°C.

The above-mentioned 5-bromo-2-hydroxyphenoxyacetic acid is heated at about 180°C. until bubbling ceases. The product is cooled and the solid residue is crystallised from cyclohexane. There is thus obtained 6-bromo-1,4-benzodioxan-2-one, m.p. 77°–80°C.

This product is reacted with methylamine by a similar process to that described in the second part of Example 8, and there is thus obtained 5-bromo-2-hydroxyphenoxy-N-methylacetamide, m.p. 189°–191°C. (crystallised from aqueous ethanol).

This phenolic product is reacted with epichlorohydrin by a similar process to that described in the last part of Example 8, and there is thus obtained 1-(4-bromo-2-N-methylcarbamoylmethoxyphenoxy)-2,3-epoxypropane as an oil which is used without further purification.

EXAMPLE 12

The process described in Example 8 is repeated except that 1-(4-benzyloxy-2-N-methylcarbamoylmethoxyphenoxy)-2,3-epoxypropane is used as starting material in place of 1-(o-N-methylcarbamoylmethoxyphenoxy)-2,3-epoxypropane. There is thus obtained 1-isopropylamino-3-(4-benzyloxy-2-N-methylcarbamoylmethoxyphenoxy)propan-2-ol, m.p. 111°–115°C. (crystallised from toluene).

The 1-(4-benzyloxy-2-N-methylcarbamoylmethoxyphenoxy)-2,3-epoxypropane used as starting material may be obtained as follows:

A solution of 3.2 g. of 2-benzoyloxy-5-benzyloxyphenol in 20 ml. of dimethylformamide is added dropwise to a stirred suspension of 0.24 g. of sodium hydride in 10 ml. of dimethylformamide. A solution of 1.7 g. of ethyl bromoacetate in 10 ml. of dimethylformamide is then added dropwise and the mixture is stirred at room temperature for 17 hours. 500 Ml. of water are added and the mixture is extracted three times with 200 ml. of ethyl acetate each time. The combined ethyl acetate extracts are washed three times with 400 ml. of water each time, dried and evaporated to dryness. The residual brown oil is partially purified by crystallisation from cyclohexane, and there is thus obtained ethyl 2-benzoyloxy-5-benzyloxyphenoxyacetate, which is used without further purification.

The above-mentioned ethyl 2-benzoyloxy-5-benzyloxyphenoxyacetate is stirred for 24 hours with 70 ml. of 30% w/v aqueous methylamine solution. The mixture is evaporated to dryness and the residue is partitioned between 80 ml. of aqueous N-sodium hydroxide solution and 80 ml. of chloroform. The aqueous extract is separated and acidified with concentrated hydrochloric acid, and the acidic mixture is extracted twice with 100 ml. of chloroform each time. The combined chloroform extracts are dried and evaporated to dryness under reduced pressure, and the residue is crystallized from ethyl acetate. There is thtus obtained 5-benzyloxy-2-hydroxy-N-methylphenoxyacetamide, m.p. 149°–152°C.

The abovementioned phenolic product is reacted with epichlorohydrin by a similar process to that described in the last part of Example 8, and there is thus obtained 1-(4-benzyloxy-2-N-methylcarbamoylmethoxyphenoxy)-2,3-epoxypropane as an oil which is used without further purification.

EXAMPLE 13

A solution of 1 g. of 1-chloro-3-(4-methyl-2-N-methylcarbamoylmethoxyphenoxy)propan-2-ol in a mixture of 20 ml. of isopropylamine and 10 ml. of methanol is heated in a sealed tube at 110°C. for 12 hours. The mixture is evaporated to dryness under reduced pressure and the residue is partitioned between 40 ml. of chloroform and 40 ml. of aqueous 2N-hydrochloric acid. The aqueous acidic layer is separated, made alkaline with solid sodium carbonate and extracted twice with 40 ml. of chloroform each time. The combined extracts are dried and evaporated to dryness under reduced pressure and the residue is crystallised from a mixture of ethyl acetate and petroleum ether (b.p. 60°–80°C.). There is thus obtained 1-isopropylamino-3-(4-methyl-2-N-methylcarbamoylmethoxyphenoxy)propan-2-ol, m.p. 101°–103°C.

The 1-chloro-3-(4-methyl-2-N-methylcarbamoylmethoxyphenoxy)propan-2-ol used as starting material may be obtained as follows:

2-Hydroxy-N,5-dimethylphenoxyacetamide, m.p. 163°–165°C. is prepared from 2-benzoyloxy-5-methylphenol by a similar process to that described in Example 12 for the preparation of 5-benzyloxy-2-hydroxy-N-methylphenoxyacetamide from 2-benzoyloxy-5-benzyloxyphenol.

A mixture of 1 g. of 2-hydroxy-N,5-dimethylphenoxyacetamiide, 10 ml. of epichlorohydrin and 3 drops of piperidine is heated at 95°–100°C. for 6 hours and then evaporated to dryness under reduced pressure. The residue consists of 1-chloro-3-(4-methyl-2-N-methylcarbamoylmethoxyphenoxy)propan-2-ol and is used without further purification.

EXAMPLE 14

A solution of 0.5 g. of 1-allylamino-3-(2-N-methylcarbamoylmethoxyphenoxy)propan-2-ol (Example 10) in 50 ml. of ethanol is shaken with 0.1 g. of a 5% palladium-on-charcoal catalyst in an atmosphere of hydrogen at atmospheric pressure and room temperature until uptake of hydrogen ceases. The mixture is filtered, the filtrate is evaporated to dryness and the residue is crystallised from a mixture of benzene and petroleum ether (b.p. 60°–80°C.). There is thus obtained 1-n-propylamino-3-(2-N-methylcarbamoylmethoxyphenoxy)propan-2-ol, m.p. 114°–115°C.

There are similarly obtained 1-isopropylamino-3-(2-N-propylcarbamoylmethoxyphenoxy)propan-2-ol, m.p. 89°–90°C. from 1-isopropylamino-3-(2-N-allylcarbamoylmethoxyphenoxy)propan-2-ol (Example 9), and 1-isopropylamino-3-(4-hydroxy-2-N-methylcarbamoylmethoxyphenoxy)propan-2-ol, m.p. 104°–106°C. from 1-isopropylamino-3-(4-benzyloxy-2-N-methylcarbamoylmethoxyphenoxy)propan-2-ol (Example 12).

EXAMPLE 15

The process described in Example 8 is repeated except that 1-(4-methoxy-2-N-methylcarbamoylmethoxyphenoxy)-2,3-epoxypropane is used as starting material in place of 1-(o-N-methylcarbamoylmethoxyphenoxy)-2,3-epoxypropane. There is thus obtained 1-isopropylamino-3-(4-methoxy-2-N-methylcarbamoylmethoxyphenoxy)propan-2-ol, m.p. 80°–82°C. (crystallised from a mixture of ethyl acetate and petroleum ether, b.p. 60°–80°C.).

The 1-(4-methoxy-2-N-methylcarbamoylmethoxyphenoxy)-2,3-epoxypropane used as starting material may be obtained by a similar process to that described in the second, third and fourth parts of Example 12, except that 2-benzoyloxy-5-methoxyphenol is used in place of 2-benzoyloxy-5-benzyloxyphenol. The 2-hydroxy-5-methoxy-N-methylphenoxyacetamide obtained as intermediate has m.p. 136°–138°C. (crystallised from water).

EXAMPLE 16

The process described in Example 8 is repeated except that 1-(o-N-ethylcarbamoylmethoxyphenoxy)-2,3-epoxypropane and t-butylamine are used as starting materials. The product in free base form, which does not crystallise, is dissolved in ether, an excess of ethereal hydrogen cloride solution is added and the mixture is evaporated to dryness. The residue is boiled with benzene and the mixture is filtered. The solid residue consists of 1-t-butylamino-3-(o-N-ethylcarbamoylmethoxyphenoxy)propan-2-ol hydrochloride, m.p. 152°C.

EXAMPLE 17

The process described in Example 8 is repeated except that 1-[o-(1-N-methylcarbamoylethoxy)phenoxy]-2,3-epoxypropane is used as starting material in place of 1-(o-N-methylcarbamoylmethoxyphenoxy)-2,3-epoxypropane. There is thus obtained 1-isopropylamino-3-[o-(1-N-methylcarbamoylethoxy)phenoxy]propan-2-ol, m.p. 102°–105°C. (crystallized from ethyl acetate).

The 1-[o-(1-N-methylcarbamoylethoxy)phenoxy]-2,3-epoxypropane used as starting material may be obtained by a similar process to that described in the second and third parts of Example 8, except that 3-methyl-1,4-benzodioxan-2-one is used as starting material in place of 1,4-benzodioxan-2-one. No intermediate product is characterised.

EXAMPLE 18

The process described in Example 1 is repeated except that 1-chloro-3-(m-carbamoylmethoxyphenoxy)propan-2-ol is used as starting material in place of 1-chloro-3-(o-carbamoylmethoxyphenoxy)propan-2-ol. There is thus obtained 1-isopropylamino-3-(m-N-isopropylcarbamoylmethoxyphenoxy)propan-2-ol, m.p. 97°–100°C. (crystallised from cyclohexane).

The 1-chloro-3-(p-carbamoylmethoxyphenoxy)propan-2-ol used as starting material may be obtained by a similar process to that described in the second part of Example 1, except that m-hydroxyphenoxyacetamide (m.p. 124°–127°C. after crystallisation from water) is used as starting material in place of p-hydroxyphenoxyacetamide.

EXAMPLE 19

The process described in Example 5 is repeated except that the appropriate 1-chloro-3-(N-substitutedcarbamoylmethoxyphenoxy)propan-2-ol derivative and isopropylamine are used as starting materials. There are thus obtained the compounds described in the following table:

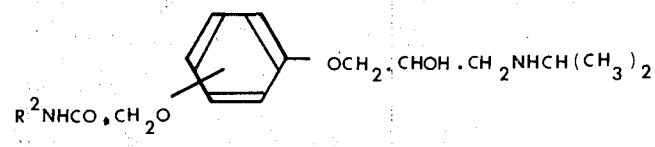

| R² | Position of R²NHCO.CH₂O— in benzene ring | m.p. (°C.) | crystallisation solvent |
| --- | --- | --- | --- |
| n-heptyl | 4- | 90–92 | ethyl acetate |
| benzyl | 4- | 102–104 | benzene |
| methyl | 3- | 62–66 | benzene/petroleum ether (b.p. 60–80°C.) |

The 1-chloro-3-(N-substituted-carbamoylmethoxyphenoxy)propan-2-ol derivatives used as starting material may be obtained from the appropriate hydroxyphenoxyacetic acid by a similar process to that described in the last part of Example 5 or Example 6. The intermediate compound m-hydroxyphenoxy-N-methylacetamide has m.p. 128°–129°C.

EXAMPLE 20

The process described in Example 5 is repeated except that 1-chloro-3-(p-3-carbamoylpropoxyphenoxy)-propan-2-ol is used as starting material in place of 1-chloro-3-(p-N-methylcarbamoylmethoxyphenoxy)propan-2-ol. There is thus obtained 1-isopropylamino-3-(p-3-carbamoylpropoxyphenoxy)propan-2-ol, m.p. 107°–110°C. (crystallised from ethyl acetate).

The 1-chloro13-(p-3-carbamoylpropoxyphenoxy)-propan-2-ol used as starting material may be obtained from ethyl 3-p-hydroxyphenoxybutyrate, ammonia and epichlorohydrin by similar processes to those described in the second and third parts of Example 5. The intermediate 3-p-hydroxyphenoxybutyramide has m.p. 119°–121°C. (crystallised from water).

EXAMPLE 21

A mixture of 1.3 g. of 3-(o-N-methylcarbamoylmethoxyphenoxy)-1-t-butylaminopropan-2-ol, 20 ml. of absolute ethanol and 2 ml. of aqueous 36% w/v formaldehyde solution is heated under reflux for 24 hours. The solution is evaporated to dryness under reduced pressure and there is thus obtained as the residual oil 5-(o-N-methylcarbamoylmethoxyphenoxymethyl)-3-t-butyloxazolidine which is characterised by its proton magnetic resonance spectrum.

EXAMPLE 22

A mixture of 1.0 g. of 1-(2-bromo-4-carbamoylmethoxyphenoxy)-2,3-epoxypropane, 10 ml. of methanol and 25 ml. of isopropylamine is kept at room temperature for 48 hours and then evaporated to dryness. The residue is crystallised from isopropanol and there is thus obtained 1-(2-bromo-4-carbamoylmethoxyphenoxy)-3-isopropylaminopropan-2-ol, m.p. 159°–161°C.

The 1-(2-bromo-4-carbamoylmethoxyphenoxy)-2,3-epoxypropane used as starting material may be obtained as follows:

A solution of 0.55 ml. of bromine in 10 ml. of glacial acetic acid is added dropwise to a cooled stirred suspension of 1.7 g. of p-hydroxyphenoxyacetic acid in 25 ml. of glacial acetic acid and the mixture is stirred for 20 hours and then filtered. The solid is crystallised from water and there is thus obtained 3-bromo-4-hydroxyphenoxyacetic acid, m.p. 189°–191°C. A mixture of 2.0 g. of this acid, 40 ml. of methanol and 0.5 ml. of concentrated sulphuric acid is heated under reflux for 4 hours and then evaporated until about 10 ml. remains. The residue is partitioned between 50 ml. of ethyl acetate and 20 ml. of water and the ethyl acetate layer is washed with saturated sodium bicarbonate solution, dried and evaporated to dryness. The solid residue is crystallised from toluene and there is thus obtained methyl-3-bromo-4-hydroxyphenoxyacetate, m.p. 72°–74°C.

A solution of 1.3 g. of this ester in aqueous ammonium hydroxide solution (specific gravity 0.88) is kept at room temperature for 24 hours and then evaporated to dryness. The residue is crystallised from water and there is thus obtained 3-bromo-4-hydroxyphenoxyacetamide, m.p. 146°–148°C. A mixture of 1 g. of this amide, 10 ml. of epichlorohydrin and 3 drops of piperidine is heated at 95°–100°C. for 7 hours and is then evaporated to dryness. The residue, which consists essentially of 3-chloro-1-(2-bromo-4-carbamoylmethoxyphenoxy)-propan-2-ol, is shaken for 4 hours with 10 ml. of aqueous N-sodium hydroxide solution. The mixture is extracted with chloroform and the chloroform extract is dried and evaporated to dryness. The residue consists of 1-(2-bromo-4-carbamoylmethoxyphenoxy)-2,3-epoxypropane as a white solid which is used without further purification.

EXAMPLE 23

The process described in Example 7 is repeated except that 1-(4-carbamoylmethoxy-2-methylphenoxy)-3-chloro-2-propanol is used as starting material in place of 1-(4-carbamoylmethoxy-2-methoxyphenoxy)-3-chloro-2-propanol. There is thus obtained 1-(4-carbamoylmethoxy-2-methylphenoxy)-3-isopropylamino-2-propanol, m.p. 146°–148°C. (crystallised from ethyl acetate).

The 1-(4-carbamoylmethoxy-2-methylphenoxy)-3-chloro-2-propanol used as starting material may be obtained by a similar process to that described in the second part of Example 7, except that 4-benzyloxy-3-methylphenol is used as starting material in place of 4-benzyloxy-3-methoxyphenol. The intermediate 4-hydroxy-3-methylphenoxyacetamide has m.p. 102°–105°C. after crystallisation from water.

EXAMPLE 24

A mixture of 3.34 g. of 4-hydroxyphenoxyacetamide, 1.6 g. of sodium hydroxide, 4 g. of 1-chloro-3-t-butylaminopropan-2-ol hydrochloride and 100 ml. of ethanol is heated under reflux for 24 hours and then filtered, and the filtrate is evaporated to dryness under reduced pressure. The residue is partitioned between 100 ml. of ethyl acetate and 50 ml. of aqueous N-sodium hydroxide solution and the organic layer is separated, washed five times with 20 ml. of water each time, dried and evaporated to dryness. The solid residue is crysytallised from a mixture of ethyl acetate and petroleum ether (b.p. 60°–80°C.) and there is thus obtained 1-(4-carbamoylmethoxyphenoxy)-3-t-butylaminopropan-2-ol, m.p. 88°–90°C.

EXAMPLE 25

A solution of 0.8 g. of 1-(N-benzyl-N-isopropylamino)- 3-(o-N-methylcarbamoylmethoxyphenoxy)propan-2-ol in 20 ml. of ethanol containing 0.5 ml. of concentrated hydrochloric acid is shaken with 50 mg. of a 5% palladium-on-charcoal catalyst in an atmosphere of hydrogen at atmospheric pressure and laboratory temperatures until the uptake of hydrogen ceases. The mixture is filtered and the filtrate is evaporated to dryness. The residue is partitioned between 10 ml. of water and 5 ml. of chloroform and the aqueous layer is separted and basified with solid sodium carbonate. The resulting emulsion is extracted twice with 25 ml. of chloroform each time and the combined extracts are dried and evaporated to dryness. The residue is crystallised from ethyl acetate and there is thus obtained 1-isopropylamino-3-(o-N-methylcarbamoylmethoxyphenoxy)propan-2-ol which is identical with the material described in Example 8.

The 1-(N-benzyl-N-isopropylamino)-3-(o-N-methylcarbamoylmethoxyphenoxy)propan12-ol used as starting material may be obtained, as an oil, by a similar process to that described in Example 8, except that a methanolic solution of N-benzylisopropylamine is used as starting material in place of isopropylamine.

EXAMPLE 26

A mixture of 0.6 g. of 3-amino-1-(o-N-methylcarbamoylmethoxyphenoxy)propan-2-ol, 20 ml. of ethanol and 20 ml. of dry acetone is shaken with 0.05 g. of a 5% palladium-on-charcoal catalyst in an atmosphere of hydrogen, at a pressure of 50 atmospheres and a temperature of 50°C. for 24 hours. The mixture is filtered and the filtrate is evaporated to dryness. The residue is crystallised from ethyl acetate and there is thus obtained 1-isopropylamino-3-(o-N-methylcarbamoylmethoxyphenoxy)propan-2-ol, which is identical with the material described in Example 8.

EXAMPLE 27

1-(4-Ethoxycarbonylmethoxyphenoxy)-3-isopropylaminopropan-2-ol (0.4 g.) is added to a stirred 25–30% w/v aqueous solution of methylamine (20 ml.) at room temperature and the mixture is allowed to stand for 16 hours and then evaporated to dryness. The residual solid is crystallised from ethyl acetate and there is thus obtained 3-isopropylamino-1-(p-N-methylcarbamoylmethoxyphenoxy)propan-2-ol, m.p. 127°–130°C.

The 1-(4-ethoxycarbonylmethoxyphenoxy)-3-isopropylaminopropan-2-ol used as starting material may be obtained as follows:

Hydrogen chloride gas is passed during 5 hours through a stirred solution of 1.7 g. of 1-(4-carbamoylmethoxyphenoxy)-3-isopropylaminopropan-2-ol in 100 ml. of absolute ethanol which is heated under reflux, at such a rate that the solution remains saturated with hydrogen chloride. The mixture is evaporated to dryness, the residue is dissolved in 50 ml. of water and the solution is basified with solid sodium carbonate to pH 9–10 and then extracted three times with 25 ml. of ethyl acetate each time. The combined extracts are dried over magnesium sulphate and evaporated to dryness and the residue is crystallised from cyclohexane. There is thus obtained 1-(4-ethoxycarbonylmethoxyphenoxy)-3-isopropylaminopropan-2-ol, m.p. 61°–63°C.

EXAMPLE 28

A solution of 2 g. of 1-(o-N-methylcarbamoylmethoxyphenoxy)-2,3-epoxybutane and 25 ml. of isopropylamine in 25 ml. of propanol is heated at 95°–100°C. for 12 hours. The mixture is evaporated to dryness and the residue is partitioned between 50 ml. of chloroform and 50 ml. of aqueous 2N-hydrochloric acid. The aqueous acidic layer is separated, made alkaline with aqueous 2N-sodium hydroxide and extracted twice with 50 ml. of chloroform each time. The combined extracts are dried and evaporated to dryness and the residue is converted into the hydrochloride thereof by conventional means. There is thus obtained 3-isopropylamino-1-(o-N-methylcarbamoylmethoxyphenoxy)butan-2-ol hydrochloride, m.p. 184°–186°C. (crystallised from a mixture of ethanol and ether).

The process described above is repeated except that t-butylamine is used in place of isopropylamine. There is thus obtained 3-t-butylamino-1-(o-N-methylcarbamoylmethoxyphenoxy)butan-2-ol hydrochloride, m.p. 177°–179°C. (crystallised from a mixture of ethanol and ether).

The 1-(o-N-methylcarbamoylmethoxyphenoxy)-2,3-epoxybutane used as a starting material may be obtained as follows:

A mixture of 3.6 g. of N-methyl-o-hydroxyphenoxyacetamide, 3.7 g. of 3-bromo-1,2-epoxybutane and 0.9 g. of sodium hydroxide in 40 ml. of water is stirred for 12 hours. The mixture is extracted twice with 50 ml. of chloroform each time. The combined extracts are dried and evaporated to dryness. the residual oil consists of 1-(o-N-methylcarbamoylmethoxyphenoxy)-2,3-epoxybutane and is used without further purification.

EXAMPLE 29

The process described in Example 14 is repeated except that 1-t-butylamino-3 -(2-N-allylcarbamoylmethoxyphenoxy)-propan-2-ol (Example 10) is used as starting material. There is thus obtained 1-t-butylamino-3-(2-N-n-propylcarbamoylmethoxyphenoxy)propan-2-ol as an oil, the structure of which is confirmed by proton magnetic resonance spectroscopy.

What we claim is:

1. A method for the treatment of angina pectoris, cardiac arrythmias, hypertension or phaeochromocytoma in a warm blooded animal in need of such treatment which comprises administering orally or intravenously to said animal an effective amount of the compound 1-t-butylamino -3-(o-N-methylcarbamoylmethoxyphenoxy) propan-2-ol or a non-toxic, pharmaceutically acceptable acid addition salt thereof.

2. A method for producing coronary beta adrenergic blockade in a warm blooded animal in need of such blockade which comprises administering orally or intravenously to said animal an effective amount of 1-t-butylamino -3-(o-N-methylcarbamoylmethoxyphenoxy) propan-2-ol or a non-toxic pharmaceutically-acceptable acid-addition salt thereof.

* * * * *